US00PP30546P2

(12) United States Plant Patent
Klemm et al.

(10) Patent No.: US PP30,546 P2
(45) Date of Patent: May 28, 2019

(54) ***OSTEOSPERMUM* PLANT NAMED 'KLEOE17330'**

(50) Latin Name: *Osteospermum ecklonis*
Varietal Denomination: KLEOE17330

(71) Applicant: Klemm+Sohn GmbH & Co. KG, Stuttgart (DE)

(72) Inventors: Nils Klemm, Stuttgart (DE); Maike Boxriker, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 15/998,065

(22) Filed: Jun. 21, 2018

(51) Int. Cl.
*A01H 5/02* (2018.01)

(52) U.S. Cl.
USPC ..... Plt./360

(58) Field of Classification Search
USPC ..... Plt./360
See application file for complete search history.

*Primary Examiner* — Annette H Para
(74) *Attorney, Agent, or Firm* — Barbara Campbell; Bethany R. Roahrig; Cochran Freund & Young LLC

(57) ABSTRACT

A new *Osteospermum* plant particularly distinguished by greyed-orange flowers with red-purple eyes and an upright growth habit, is disclosed.

1 Drawing Sheet

Genus and species: *Osteospermum ecklonis.*
Variety denomination: 'KLEOE17330'.

BACKGROUND OF THE NEW PLANT

The present invention comprises a new and distinct variety of *Osteospermum*, botanically known as *Osteospermum ecklonis*, and hereinafter referred to by the variety name 'KLEOE17330'. 'KLEOE17330' originated from a cross-pollination conducted in May to October 2013 in Nairobi, Kenya between the proprietary female *Osteospermum* variety 'OE-2012-0402' (unpatented), and the male *Osteospermum* variety SUNNY 'Cilia' (patent status unknown).

The seeds from the cross were sown and plants were grown in a greenhouse for evaluation, where an individual plant designated 'KLEOE17330' was selected from the group of plants in May 2014 in Stuttgart, Germany. In October 2014 in Stuttgart, Germany, 'KLEOE17330' was first vegetatively propagated by vegetative terminal cuttings. 'KLEOE17330' was found to reproduce true to type in successive generations of asexual propagation via vegetative terminal cuttings.

SUMMARY

The following are the most outstanding and distinguishing characteristics of this new variety when grown under normal horticultural practices in Stuttgart, Germany.

1. Greyed-orange flowers with red-purple eyes; and
2. An upright growth habit.

DESCRIPTION OF THE PHOTOGRAPH

This new *Osteospermum* plant is illustrated by the accompanying photograph which shows the plant's overall plant habit including form, foliage, and flowers. The photograph is of a 9-week-old plant grown in a greenhouse in Stuttgart, Germany in April 2016. The colors shown are as true as can be reasonably obtained by conventional photographic procedures.

DESCRIPTION OF THE NEW VARIETY

The following detailed descriptions set forth the distinctive characteristics of 'KLEOE17330'. The data which define these characteristics were collected on plants after 11 weeks (at the time of flowering) in Stuttgart, Germany in April 2018. The plants were treated with CYCOCEL three times. Color references are to The R.H.S. Colour Chart of The Royal Horticultural Society of London (R.H.S.), 5$^{th}$ edition (2007).

Classification:
- *Family.*—Asteraceae.
- *Botanical.*—*Osteospermum ecklonis.*
- *Common.*—*Osteospermum.*
- *Designation.*—'KLEOE17330'.

Parentage:
- *Female parent.*—The proprietary female *Osteospermum* variety 'OE-2012-0402' (unpatented).
- *Male parent.*—The male *Osteospermum* variety SUNNY 'Cilia' (patent status unknown).

Plant:
- *Form and habit.*—Herbaceous perennial but usually cultivated as an annual; not frost resistant.
- *Growth habit.*—Upright.
- *Branching habit.*—Normal.
- *Height (from top of soil, including inflorescence).*—13.0 cm.
- *Width (including inflorescences).*—14.0 cm.
- *Propagation type.*—Stem cuttings; vegetative terminal tip cuttings.
- *Time to produce a finished flowering plant.*—About 9 weeks.
- *Time to initiate and develop roots.*—3 to 4 weeks.
- *Root description.*—Light tan in color, fine.

Stems:
- *Total number of branches per plant (calculated at the base of the plant).*—4.
- *Length.*—9.0 cm.
- *Diameter.*—0.2 cm.
- *Internode length.*—1.0 cm.

*Color*.—RHS 144A (Yellow-green).
*Texture*.—Smooth, but with fine hairs.
*Anthocyanin*.—RHS 187A (Greyed-purple).

Leaves:
*Arrangement*.—Alternate.
*Shape*.—Oblanceolate.
*Apex*.—Acute.
*Base*.—Acute.
*Immature color*.—Upper surface: RHS 137A (Green). Lower surface: RHS 137C (Green).
*Mature color*.—Upper surface: RHS 137B (Green). Lower surface: RHS 137C (Green). Length: 3.5 cm. Width: 1.0 cm.
*Texture* (*both upper and lower surfaces*).—Leathery.
*Petioles*.—Absent.
*Venation pattern*.—Pinnate.
*Venation color*.—Upper surface: RHS 137C (Green). Lower surface: RHS 143A (Green).

Flower buds:
*Shape*.—Round-ovoid.
*Apex*.—Obtuse.
*Base*.—Acute.
*Margin*.—Entire.
*Texture*.—Smooth with fine hairs.
*Length*.—1.5 cm.
*Diameter*.—1.1 cm.
*Color* (*at tight bud just before the ray florets unfold*) .—RHS 145A (Yellow-green).

Inflorescence:
*Type*.—Composite, single.
*Blooming habit*.—Upright.
*Quantity of inflorescences per plant*.—4.
*Lastingness of the inflorescences on the plant*.—10 to 15 days.
*Fragrance*.—Slight.
*Inflorescence diameter*.—5.8 cm.
*Inflorescence depth*.—1.5 cm.

Disc floret:
*Quantity per inflorescence*.—About 30.
*Shape*.—Tubular.
*Tube color*.—Closed: RHS 155A (White). Mature: RHS 59A (Red-purple).
*Length*.—0.6 cm.
*Diameter* (*at apex*).—0.2 cm.
*Apex*.—Acute.
*Apex color*.—RHS 59A (Red-purple).
*Base*.—Acute.
*Base color*.—RHS 160B (Greyed-yellow).
*Margin*.—Entire.

Ray floret:
*Quantity per inflorescence*.—22.
*Shape*.—Oblanceolate.
*Color*.—Upper surface: RHS N172A (Greyed-orange) on the outer parts and RHS 64A (Red-purple) on the inner part. Lower surface: RHS 165B (Greyed-orange).
*Length*.—3.0 cm.
*Width*.—0.7 cm.
*Apex*.—Acute.
*Base*.—Acute.
*Margin*.—Entire.
*Texture*.—Upper surface: Smooth. Lower surface: Smooth, shiny.

Peduncle:
*Length*.—9.0 cm.
*Diameter*.—0.2 cm.
*Texture*.—Smooth with hairs.
*Color*.—RHS143B (Green).

Phyllaries:
*Arrangement*.—Single.
*Observed quantity per flower*.—22.
*Shape*.—Lanceolate.
*Apex*.—Acute.
*Base*.—Obtuse.
*Margin*.—Entire.
*Length*.—1.1 cm.
*Width*.—0.1 cm.
*Texture*.—Upper surface: Smooth with fine hairs. Lower surface: Smooth.
*Color*.—Upper surface: RHS 143C (Green). Lower surface: RHS 145A (Yellow-green).

Reproductive organs:
*Androecium*.—Location: On disc and ray florets. Stamens: Shape: Filamentous. Quantity: Numerous. Filament length: 0.4 cm. Filament diameter: Greater than 0.1 cm. Anther: Shape: Lanceolate. Color: RHS N77A (Purple). Length: 0.1 cm. Diameter: Greater than 0.1 cm. Pollen: Color: RHS 21A (Yellow-orange). Amount: Moderate.
*Gynoecium*.—Location: On the phyllary. Pistils: Number: Numerous. Length: 0.6 cm. Diameter: Greater than 0.1 cm. Stigma: Color: RHS N79A (Purple). Shape: Tapering filamentous and split in two parts. Length: 0.1 cm. Diameter: Greater than 0.1 cm. Style: Color: RHS 157B (Green-white). Length: 0.5 cm. Diameter: Greater than 0.1 cm.

Fruit and seed set: None observed.

Disease and pest/insect resistance: No disease and pest/insect resistance observed.

COMPARISON WITH PARENTAL LINES AND KNOWN VARIETY

'KLEOE17330' is a distinct variety of *Osteospermum* and is distinguished from its parents as described in Table 1.

TABLE 1

Comparison with Parental Lines

| Characteristic | 'KLEOE17330' | Female Parent 'OE-2012-0402' | Male Parent SUNNY 'Cilia' |
|---|---|---|---|
| Flower Color | Greyed-orange with red-purple eye | Red | Orange |

'KLEOE17330' is most similar to the commercial *Osteospermum* variety 'KLEOE03103' (unpatented). Differences between the varieties are described in Table 2.

TABLE 2

Comparison with Similar Variety

| Characteristic | 'KLEOE17330' | 'KLEOE03103' |
|---|---|---|
| Flower color | Greyed-orange with red-purple eye | Pink with white eyes |

We claim:

1. A new and distinct variety of *Osteospermum* plant designated 'KLEOE17330' as illustrated and described herein.

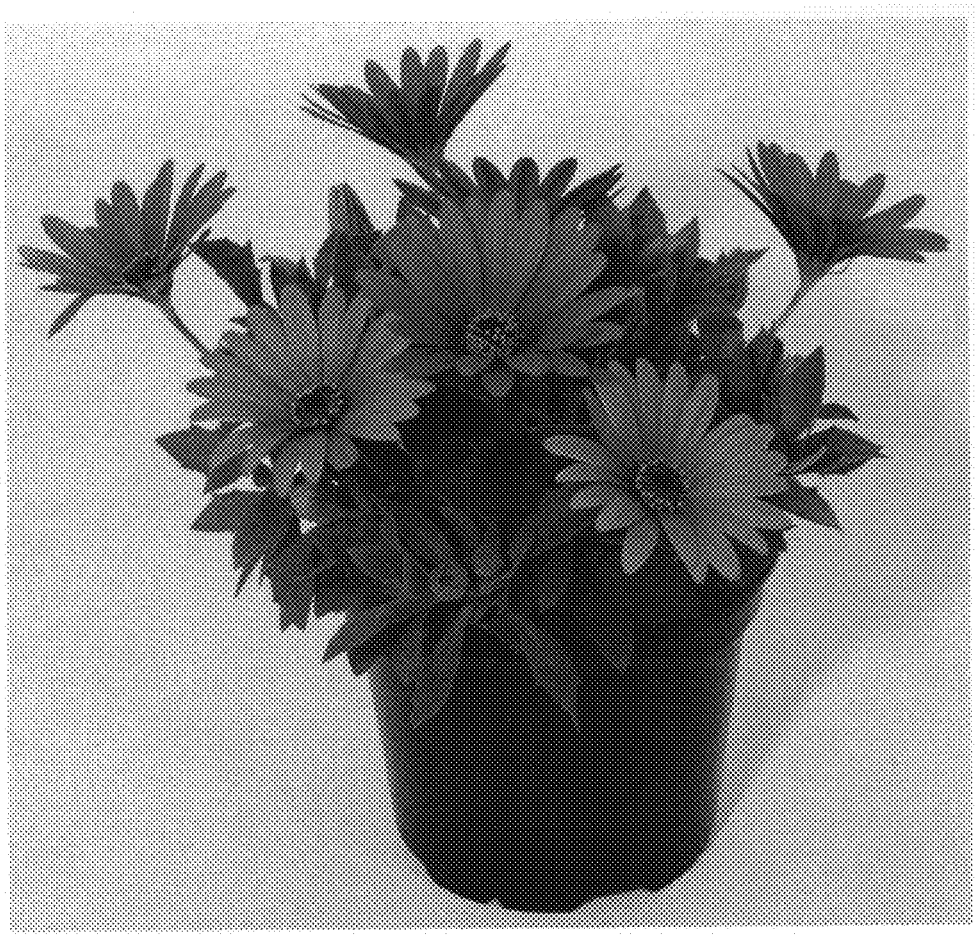

* * * * *